United States Patent [19]
Jayaraman

[11] Patent Number: 5,893,887
[45] Date of Patent: Apr. 13, 1999

[54] STENT FOR POSITIONING AT JUNCTION OF BIFURCATED BLOOD VESSEL AND METHOD OF MAKING

[75] Inventor: Swaminathan Jayaraman, Dallas, Tex.

[73] Assignee: Iowa-India Investments Company Limited, United Kingdom

[21] Appl. No.: 08/949,549

[22] Filed: Oct. 14, 1997

[51] Int. Cl.$^6$ ............................................. A61F 2/06
[52] U.S. Cl. ............................................. 623/1
[58] Field of Search ........................... 623/1, 11, 12

[56] References Cited

U.S. PATENT DOCUMENTS

| | | |
|---|---|---|
| 3,155,095 | 11/1964 | Brown ............................ 623/1 |
| 4,441,215 | 4/1984 | Kaster ............................ 623/1 |
| 4,994,071 | 2/1991 | MacGregor . | |
| 5,102,417 | 4/1992 | Palmaz ............................ 623/1 |
| 5,127,919 | 7/1992 | Ibrahim ............................ 623/1 |
| 5,156,619 | 10/1992 | Ehrenfeld ........................ 623/1 |
| 5,489,295 | 2/1996 | Piplanie et al. . | |
| 5,507,767 | 4/1996 | Maeda ............................ 623/1 |
| 5,514,178 | 5/1996 | Torchio ............................ 623/1 |
| 5,667,486 | 9/1997 | Mikulich ........................ 623/1 |

FOREIGN PATENT DOCUMENTS 4032759  4/1992  Germany ......................... 623/1

*Primary Examiner*—Michael J. Milano
*Attorney, Agent, or Firm*—Larson & Larson, P.A.; James E. Larson

[57] ABSTRACT

A stent has a generally cylindrical shape having a series of slots or other surface discontinuities facilitating adherence to the inner walls of a blood vessel. In one embodiment, one end of the stent has a terminus that is tapered at a non-orthogonal angle with respect to the axis of elongation of the stent. In other embodiments, both ends are angled non-orthogonally with respect to the longitudinal axis of the stent. The particular angle that each end surface of the stent makes with the longitudinal axis of the stent may be varied, in each case, to accommodate to bifurcated blood vessels of varying sizes, shapes and configurations. Use of stents in accordance with the teachings of the present invention precludes wall portions of a stent from protruding into a passage of a blood vessel in a manner that would cause restricted flow through the blood vessel. The method of making the stent in accordance with the teachings of the present invention is also disclosed.

8 Claims, 4 Drawing Sheets

STENT FOR POSITIONING AT JUNCTION OF BIFURCATED BLOOD VESSEL AND METHOD OF MAKING

BACKGROUND OF THE INVENTION

The present invention relates to a stent for positioning at a junction of a bifurcated blood vessel and the method of making such a stent. In the prior art, stents are well known and are commonly surgically implanted within blood vessels, whether arteries or veins, particularly at the conclusion of a surgical procedure known as a balloon angioplasty, which procedure is employed to flatten arteriosclerosis induced deposits against the vessel wall, with the stent thereafter being implanted at the surgical site to deter and preclude narrowing of the flow passage through the blood vessel at the location where the stent is implanted.

It is well known to make a stent having a generally cylindrical tubular body shape having slots or other surface irregularities therethrough promoting adherence of the stent in the implanted location. It is also well known to make stents having end surfaces that are generally perpendicular to the axis of elongation of the stent body itself. Such stents are useful when implanted within blood vessels in areas not adjacent to a junction with another blood vessel or other type of bifurcation. Where implantation of a stent is required at an area of bifurcation of a blood vessel or other junction location therein, use of a stent having end surfaces perpendicular to the axis of elongation of the stent may be detrimental to the patient's recovery.

In this regard, when such a prior art stent is employed at a blood vessel junction or bifurcation, one "corner" of the stent may protrude into the adjacent blood vessel thereby interfering with smooth blood flow therethrough. Thus, while the stent is curing one problem in the blood vessel where it has been implanted, at the same time, it can be causing a new problem in the adjacent blood vessel by restricting flow, sometimes to a degree that might be analogous to the result of an advanced case of arterio-sclerosis.

Thus, a need has developed for a stent having a configuration facilitating implantation at a junction or bifurcation in a blood vessel so that the blood vessel where the stent is implanted is effectively treated while, at the same time, the adjacent or joining blood vessel suffers no ill effects as a result thereof. It is with this need in mind that the present invention was developed.

SUMMARY OF THE INVENTION

The present invention relates to a stent for positioning at the junction of a bifurcated blood vessel and the method of making such a stent. The present invention includes the following interrelated objects, aspects and features:

(1) In a first aspect, in the embodiments of the inventive stent disclosed herein, the stent is made in a generally cylindrical shape. One manner of making a stent in accordance with the teachings of the present invention consists of providing a flat piece of material with slots cut therein by any suitable process such as, for example, through use of a laser cutting machine, a chemical etching machine, an electron beam cutting machine or any other suitable device. Other types of surface irregularities designed to facilitate adherence of the stent in implanted position may be suitably substituted for such slots. With the flat piece of material so created, in a generally rectangular shape, corners of the piece of material are removed in a manner depending upon the particular desired degree of taper of the respective end surfaces of the finished stent. Thereafter, the piece of material is rolled upon itself with the facing side walls affixed together to form a tubular stent having end surfaces tapered as desired. Another manner of making a stent in accordance with the teachings of the present invention consists of providing a tubular piece of material with slots cut therein by any of the same processes used in cutting slots in the flat piece of material stated herein above.

(2) In one embodiment of the present invention, one end of the stent has an end surface that is generally perpendicular to the axis of elongation of the stent. The other end surface thereof is angled obliquely and non-orthogonally with respect to the axis of elongation of the stent.

(3) In a second embodiment of the present invention, both end surfaces of the stent are angled non-orthogonally with respect to the axis of elongation of the stent. In this embodiment, both end surfaces are angled in the same direction, although their respective degrees of obliqueness with respect to the axis of elongation of the stent may be different.

(4) In a third embodiment of the present invention, both end surfaces are angled obliquely with respect to the axis of elongation of the stent but in opposed directions.

(5) One or both end surfaces may define an angle of 30°, 45°, 60° or other oblique angle with respect to the axis of elongation of the stent. If desired, the end surfaces may be coated with a radio-opaque material so that they may be easily viewed for accurate positioning in a bifurcated blood vessel.

(6) Any of the three above embodiments may also include varying length linkages for permitting the formation of the desired angled end surfaces.

As such, it is a first object of the present invention to provide a stent for positioning at a junction of a bifurcated blood vessel and the method of making such a stent.

It is a further object of the present invention to provide such a device wherein at least one end surface thereof is angled obliquely with respect to an axis of elongation of the stent.

It is a further object of the present invention to provide such a stent wherein both end surfaces are angled obliquely with respect to the axis of elongation thereof.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
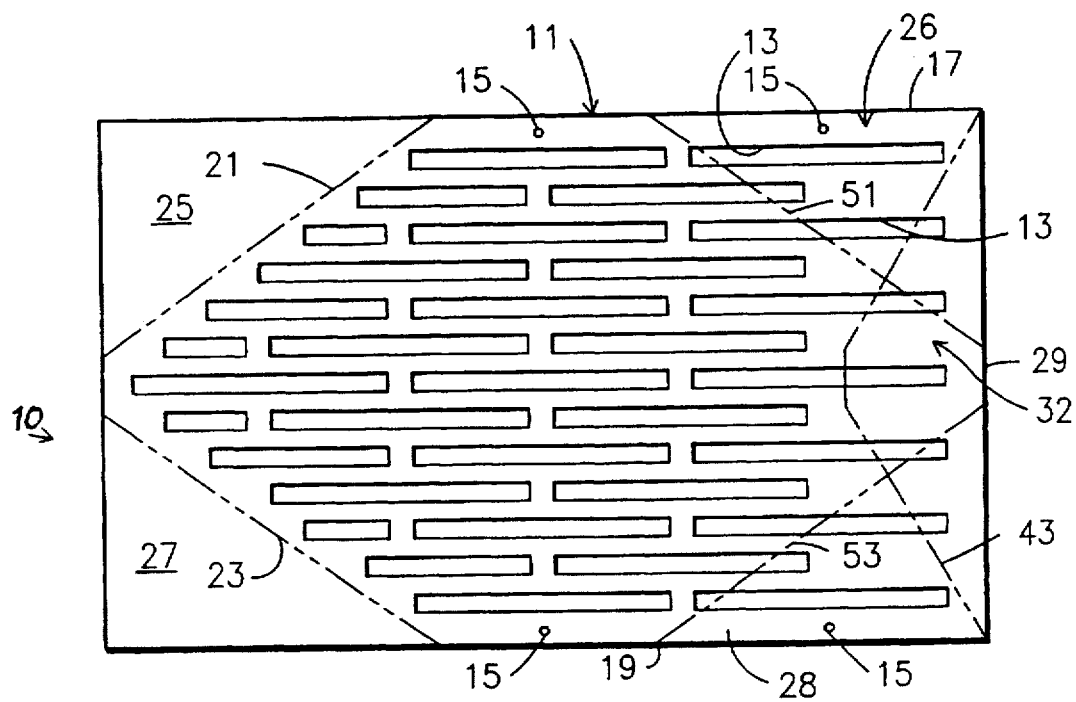
FIG. 1 shows a top view of a sheet of material to be used in creating a stent in accordance with the teachings of the present invention.
Figure 2:
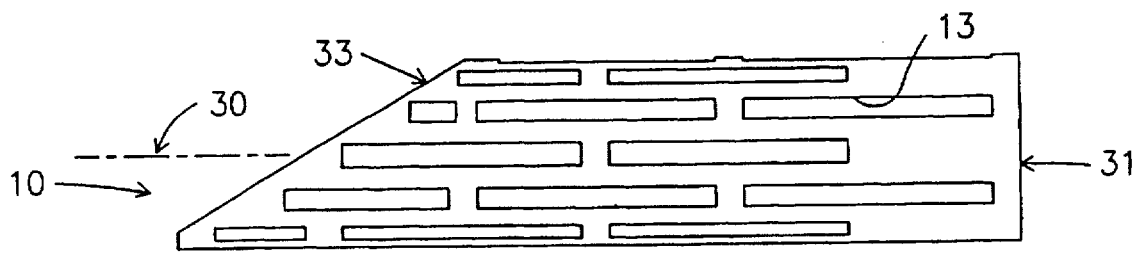
FIG. 2 shows a first embodiment of stent in accordance with the teachings of the present invention.

With reference to FIG. 2, a first embodiment of stent in accordance with the teachings of the present invention is generally designated by the reference numeral 10. In FIG. 1, it is seen that a sheet 11 has a generally rectangular shape and has a multiplicity of slots 13 cut therein in any suitable manner such as, for example, using a laser cutting machine, a chemical etching machine, an electron beam cutting machine or any other suitable device. Holes 15 are formed in the sheet 11 adjacent opposite edges 17 and 19. As should be understood, the sheet 11 may be rolled into a tubular form as seen in FIG. 2 with holes 15 aligned with one another, and fastening means such as a wire or string or other suitable means being employed to hold the stent 10 in its tubular configuration.

With further reference to FIG. 1, concerning the embodiment of FIG. 2, the dashed lines 21 and 23 indicate areas where the sheet 11 may be cut to remove the pieces of material 25 and 27, respectively. Thereafter, the sheet 11 is rolled to the configuration shown in FIG. 2 to form the finished stent 10. As seen in FIG. 2, when the sheet of material 11 is rolled into a generally cylindrical configuration, the wall 29 (FIG. 1) of the piece of material causes formation of a flat end surface 31 that is orthogonal to the axis 30 of elongation of the stent. The cut lines 21 and 23 cause formation of an end surface 33 (FIG. 2) that is angled obliquely with respect to the axis 30 of elongation of the stent 10.

Figure 3:
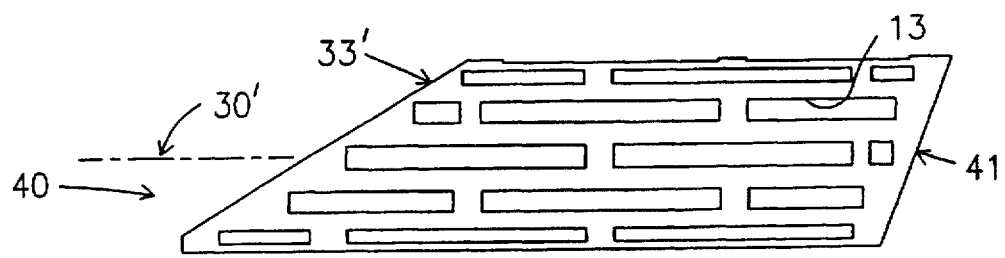
FIG. 3 shows a second embodiment thereof.

With reference to FIG. 3, wherein like elements are designated using like reference numerals, a second embodiment of the present invention is generally designated by the reference numeral 40 and is seen to depict a stent having an axis of elongation 30' as well as a surface 33' corresponding to the surface 33 of the stent best seen in FIG. 2. With reference back to FIG. 1, the dotted line 43 depicts a location on the sheet 11 where a cut may be made to remove the piece 32 of material to cause formation of the surface 41 seen in the stent 40 illustrated in FIG. 3. Thus, the stent 40 of FIG. 3 is the same as the stent 10 of FIG. 2 except that the surface 31 of the stent 10 has been replaced through formation of the cut along the line 43 of the piece of material 11 forming surface 41.

Figure 4:
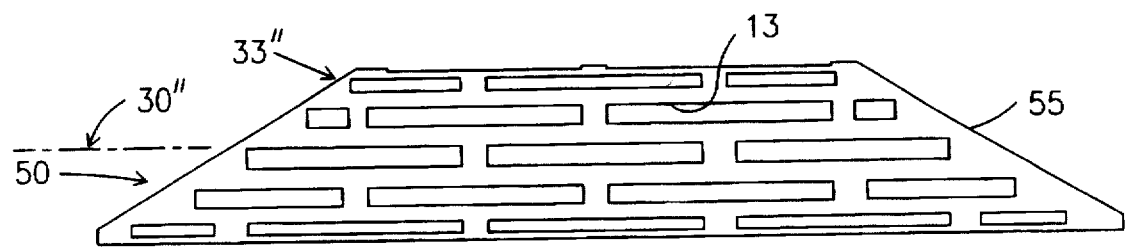
FIG. 4 shows a third embodiment thereof.

With reference to FIG. 4, a third embodiment of stent in accordance with the teachings of the present invention is generally designated by the reference numeral 50. In FIG. 4, like elements as compared to the stents 10 and 40 are designated with like double-primed reference numerals. Thus, the stent 50 has an axis of elongation 30", as well as a surface 33", formed in the same manner as the surfaces 33 and 33" of the embodiments of FIG. 2 and 3, respectively.

With reference to FIGS. 2, 3, and 4, stents 10, 40, and 50, respectively, may be made from a tubular piece of material. The multiplicity of slots 13 are cut in any suitable manner such as, for example, using a laser cutting machine, a chemical etching machine, an electron beam cutting machine or any other suitable device. End surfaces 33 and 31 of stent 10 (FIG. 2), 33' and 41 of stent 40 (FIG. 3), and 33" and 55 of stent 50 (FIG. 4) are formed by cutting a desired angled in any suitable manner.

With reference back to FIG. 1, the dotted lines 51 and 53 in the sheet 11 designate cut lines such that when the sheet 11 is cut at the lines 51 and 53, pieces of material 26 and 28, respectively, are removed and the sheet 11 is rolled up to form a cylinder with the surface 55 in FIG. 4 being formed.

Figure 7:
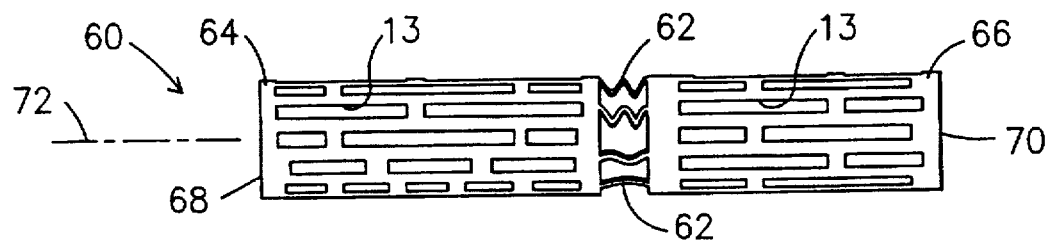
FIG. 7 shows an unexpanded alternate first embodiment of stent in accordance with the teachings of the present invention.
Figure 8:
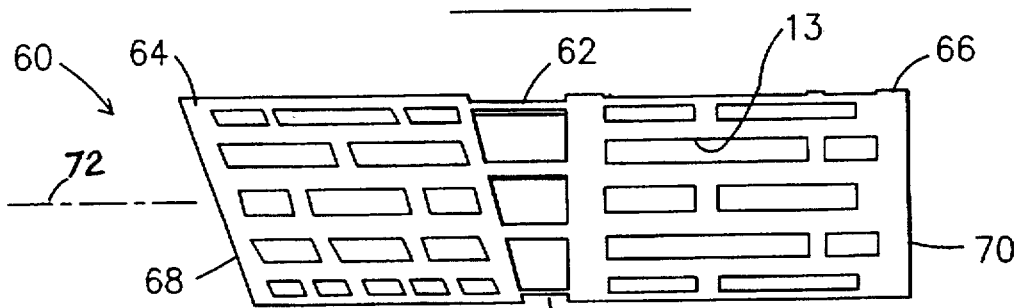
FIG. 8 shows an expanded alternate first embodiment thereof.

With reference to FIGS. 7 and 8, a alternate first embodiment of stent in accordance with the teachings of the present invention is generally designated by the reference numeral 60. FIG. 7 shows stent 60 in an unexpanded state, while FIG. 8 shows stent 60 in an expanded state.

Further to FIGS. 7 and 8, as in the preferred first embodiment, stent 60 may be formed from a rectangular or tubular piece of material. Slots 13 are cut therein in any suitable manner as those disclosed and given as examples in the preferred embodiment of stent 10. In addition, varying length linkages 62 are cut therein in any of the suitable manners. Such configuration forms a first member 64 and a second member 66 with varying length linkages 62 intermediately positioned between first and second members 64 and 66. The frequency of each varying length linkage determines the angle of opposed first and second end surfaces, 68 and 70 respectively, with respect to an axis 72 of elongation of stent 60. Accordingly, as shown in FIG. 7, linkages 62 decrease uniformly in frequency from a top portion to a bottom portion such that linkages at the top position have a shorter wave length than those at the bottom portion. Such configuration forms expanded stent 60 of FIG. 8 where first end surface 68 is angled obliquely and second end surface 70 is angled orthogonal with respect to axis 72 of elongation of stent 60.

Figure 9:
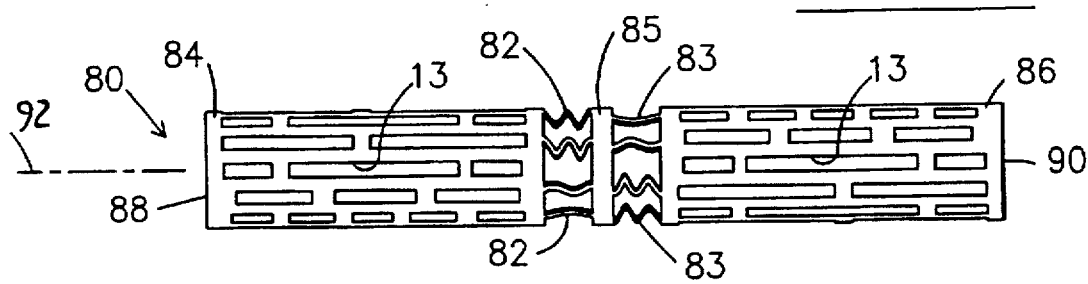
FIG. 9 shows an unexpanded alternate second embodiment thereof.
Figure 10:
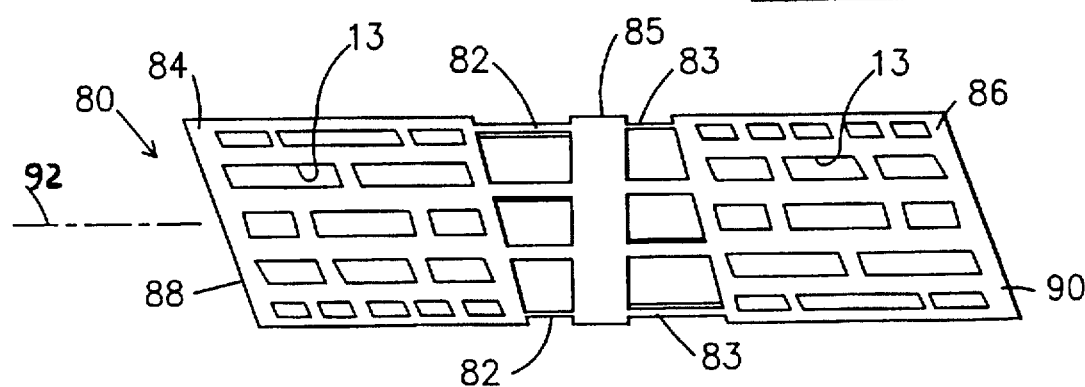
FIG. 10 shows an expanded alternate second embodiment thereof.

With reference to FIGS. 9 and 10, an alternate second embodiment of stent in accordance with the teachings of the present invention is generally designated by the reference numeral 80. FIG. 9 shows stent 80 in an unexpanded state, while FIG. 10 shows stent 80 in an expanded state.

Further to FIGS. 9 and 10, as in the preferred second embodiment, stent 80 may be formed from a rectangular or tubular piece of material. Slots 13 are cut therein in any suitable manner as those disclosed and given as examples in the preferred embodiment of stent 40. In addition, a pair of varying length linkages 82 and 83 and an intermediate member 85 are cut therein in any of the suitable manners. Such configuration forms a first member 84 and a second member 86 with varying length linkages 82 and 83 intermediately positioned between first and second members 84 and 86 and intermediate member 85 intermediately positioned between the pair of varying length linkages 82 and 83. The frequency of each varying length linkage and the decreasing or increasing wavelength of each pair of linkages determines the angle of opposed first and second end surfaces, 88 and 90 respectively, with respect to an axis 92 of elongation of stent 80. As shown in FIG. 9, linkages 82 and 83 are inversely proportional such that linkages 82 have a frequency of shorter wavelength at a top portion while linkages 83 have a frequency of shorter wavelength at a bottom portion. Linkages 82 and 83 increase or decrease uniformly in frequency, respectively, from a top to a bottom portion. Such configuration forms expanded stent 80 of FIG. 10 where first and second end surfaces 88 and 90 are angled obliquely with respect to axis 92 of elongation of stent 90. The exact frequency and increasing or decreasing wavelength value of each pair of varying length linkages 82 and 82 may be chosen to permit end surfaces 88 and 90 to be angled in the same direction and of the same degree or in the same direction but of different degree with respect to axis 92.

Figure 11:
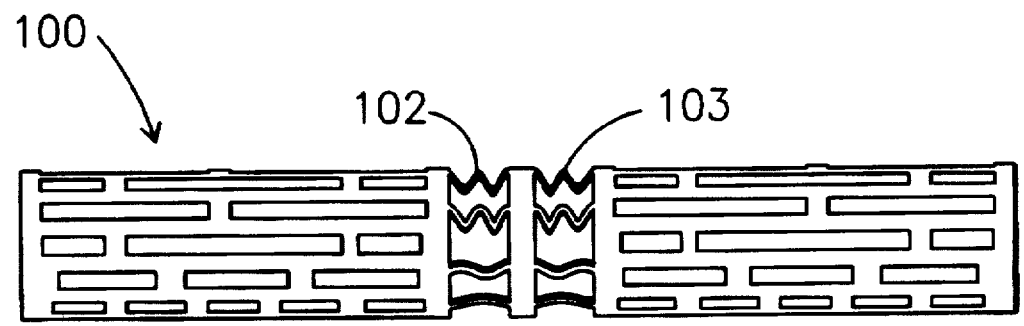
FIG. 11 shows an unexpanded alternate third embodiment thereof.
Figure 12:
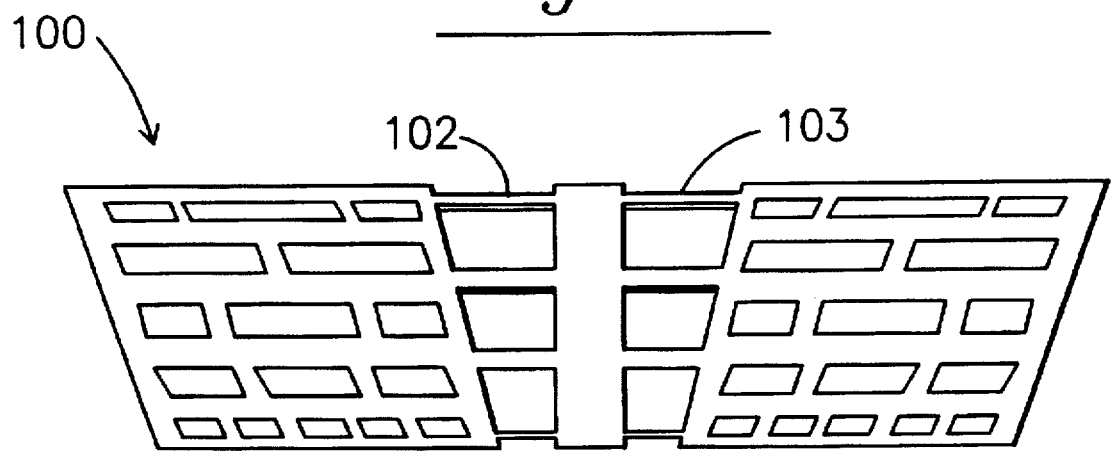
FIG. 12 shows an expanded alternate third embodiment thereof.

With reference to FIGS. 11 and 12, an alternate third embodiment of stent in accordance with the teachings of the present invention is generally designated by the reference numeral 100. FIG. 11 shows stent 100 in an unexpanded state, while FIG. 12 shows stent 100 in an expanded state.

Stent 100 is formed identically in the manner of stent 80 although stent 100 has a slightly different configuration. The purpose for stent 100 is to provide a stent having angled end surfaces of like or different degree but angled in opposed directions. Accordingly, stent 100 is provided with a pair varying length linkages 102 and 103 that have generally proportional increasing or decreasing wavelength value. As shown in FIG. 11, the frequency of linkages 102 and 103 at a top portion have a shorter wavelength than those at a bottom portion. The corresponding wavelengths in relation to linkages 102 to 103 may be varied slightly such that the angles produced at end surfaces are of the same or of different degree. FIG. 12 depicts stent 100 having end surfaces of a generally same degree but angled in opposed directions.

If a rectangular piece of material is used for stents 60, 80, or 100, holes 15 (not shown in FIGS. 7–12) are used just as in stents 10, 40, and 50.

Figure 5:
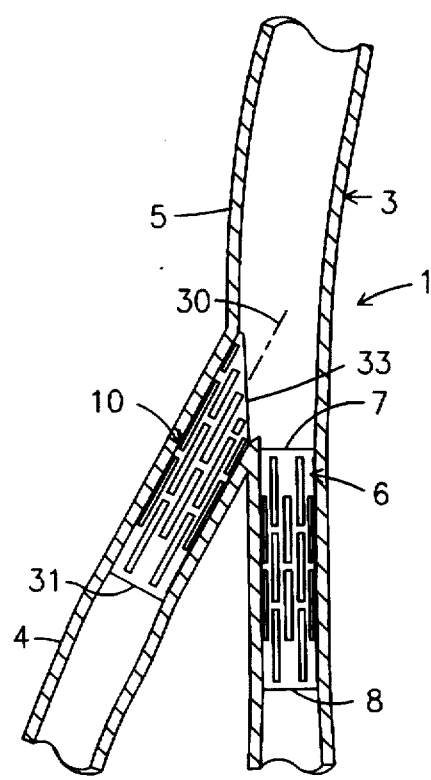
FIG. 5 shows the first embodiment illustrated in FIG. 2 as implanted within a bifurcated blood vessel.

With reference to FIG. 5, the stent 10 is seen implanted within a branch 4 of a bifurcated blood vessel 1 having a main vessel 3 from which the branch 4 extends off the wall 5 of the vessel 3. In FIG. 5, the end surfaces 31 and 33 are plainly seen with the surface 33 due to its oblique nature with respect to the axis 30 of elongation of the stent 10, precluding any significant structure of the stent 10 from protruding within the vessel 3. FIG. 5 also shows a stent 6 having perpendicular end surfaces 7 and 8 as is known in the prior art.

Figure 6:
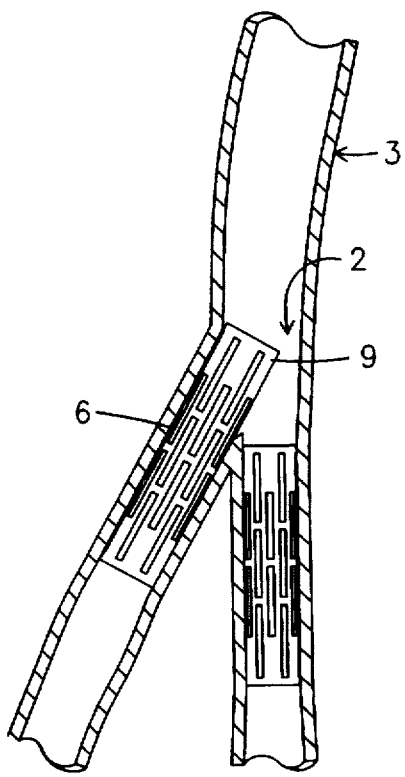
FIG. 6 shows a prior art stent implanted in a bifurcated blood vessel.

FIG. 6 shows the prior art method of using a stent 6 within a branch vessel 4 wherein a corner 9 of the stent 6 protrudes within the blood vessel 3 therefore defining a restricted orifice 2 that restricts flow of blood through the vessel 3 with a similar in effect as is the case where arterio-sclerosis has narrowed a blood vessel.

In accordance with the teachings of the present invention, such restrictions 2 are avoided at the junction of the branches of a bifurcated blood vessel such as the bifurcated blood vessel 1 shown in FIG. 5.

The three preferred embodiments and three alternate embodiments of the present invention illustrated herein are merely exemplary and are provided to demonstrate the versatility with which the teachings of the present invention may be applied to any situation that a surgeon encounters within the vascular system of a human being. With knowledge from the particular physical characteristics of a junction between two branches of a bifurcated blood vessel, the surgeon may create an appropriate stent with end surfaces specifically devised to prevent restrictions of blood flow adjacent the location of implantation of such a stent.

As such, an invention has been disclosed in terms of preferred embodiments thereof which fulfill each and every one of the objects of the present invention as set forth hereinabove and provide a new and useful stent for positioning at the junction of a bifurcated blood vessel and the method of making that have great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A stent comprising:

(a) generally cylindrical body defining an axis of elongation and first and second end surfaces, (b) at least a first, second and intermediate member, (c) at least one set of varying length linkages comprising a pair of varying length linkages intermediately disposed between said first and second member, (d) at least one of said end surfaces being angled obliquely and non-orthogonally with respect to said axis, and (e) said intermediate member intermediately disposed between said pair of varying length linkages.

2. The stent of claim 1, wherein said first and second end surfaces are angled obliquely and non-orthogonally with respect to said axis.

3. A method of making a stent including the steps of:

a) providing a rectangular piece of material having first and second ends and opposed edges;

b) cutting a multiplicity of slots in the rectangular piece of material;

c) removing two corners of said piece at one of said ends;

d) rolling said piece into a cylindrical shape; and e) attaching said opposed edges of said piece together.

4. The method of claim 3, wherein said one of said ends comprises said first end, and further including the step, before said rolling step, of removing two corners of said piece at said second end.

5. The method of claim 3, wherein said ends define end surfaces, and further including the step of coating said end surfaces with a radio-opaque material.

6. The method of claim 4, wherein said ends define end surfaces angling in opposed directions.

7. The method of claim 4, wherein said ends define end surfaces angling in a same direction.

8. A stent comprising, (a) a generally cylindrical body defining an axis of elongation and first and second end surfaces, (b) at least a first and second member, (c) at least one set of varying length linkages intermediately disposed between the at least first and second members, (d) at least one of the end surfaces being angled obliquely and non-orthogonally with respect to the axis of elongation and positioned at an area of bifurcation of a blood vessel so that the stent does not protrude into an adjacent blood vessel to interfere with smooth blood flow therethrough.

* * * * *